US00PP11297P

United States Patent [19]

Boeder

[11] Patent Number: Plant 11,297

[45] Date of Patent: Mar. 21, 2000

[54] CHRYSANTHEMUM PLANT NAMED 'TOUCAN'

[75] Inventor: Mark Boeder, West Wittering, United Kingdom

[73] Assignee: Cleangro Limited, West Sussex, United Kingdom

[21] Appl. No.: 09/038,891

[22] Filed: Mar. 11, 1998

[51] Int. Cl.[7] ..... A01H 5/00

[52] U.S. Cl. ..... Plt./286

[58] Field of Search ..... Plt./286, 287, 291, Plt./292, 297, 296, 290

[56] References Cited

U.S. PATENT DOCUMENTS

P.P. 8,803 6/1994 Fuess ..... Plt./287

*Primary Examiner*—Howard J. Locker

*Attorney, Agent, or Firm*—Christie, Parker & Hale, LLP

[57] ABSTRACT

A new plant variety of Chrysanthemum producing flowers of unusual spider daisy flower form.

2 Drawing Sheets

BACKGROUND OF THE INVENTION

The present invention is directed to a new and distinct variety of Chrysanthemum botanically classified as *Dendranthema grandiflora*. The varietal denomination of the new chrysanthemum is 'Toucan'.

The female parent of the new variety is the variety known as 'Empire Serenade' (U.S. Plant Pat. No. 8,803) and the male parent is an undistributed, unnamed seedling identified as 'G12-C1'. The new variety has been asexually reproduced by vegetative cuttings in Ventura County, Calif. and the distinguishing characteristics are retained through successive generations of asexual reproduction.

SUMMARY OF THE INVENTION

'Toucan' is a pot type Chrysanthemum plant variety that produces flowers of unusual spider daisy flower form.

Comparison With 'Empire Serenade'

'Toucan' differs from 'Empire Serenade' in having a shorter response time and different flower color.

BRIEF DESCRIPTION OF ILLUSTRATIONS

The accompanying photographs show a typical specimen of potted plant of the new variety and of flowers of the new variety, with colors being as nearly true as possible with illustrations of this type.

DESCRIPTION OF THE PLANT

Figure 1:
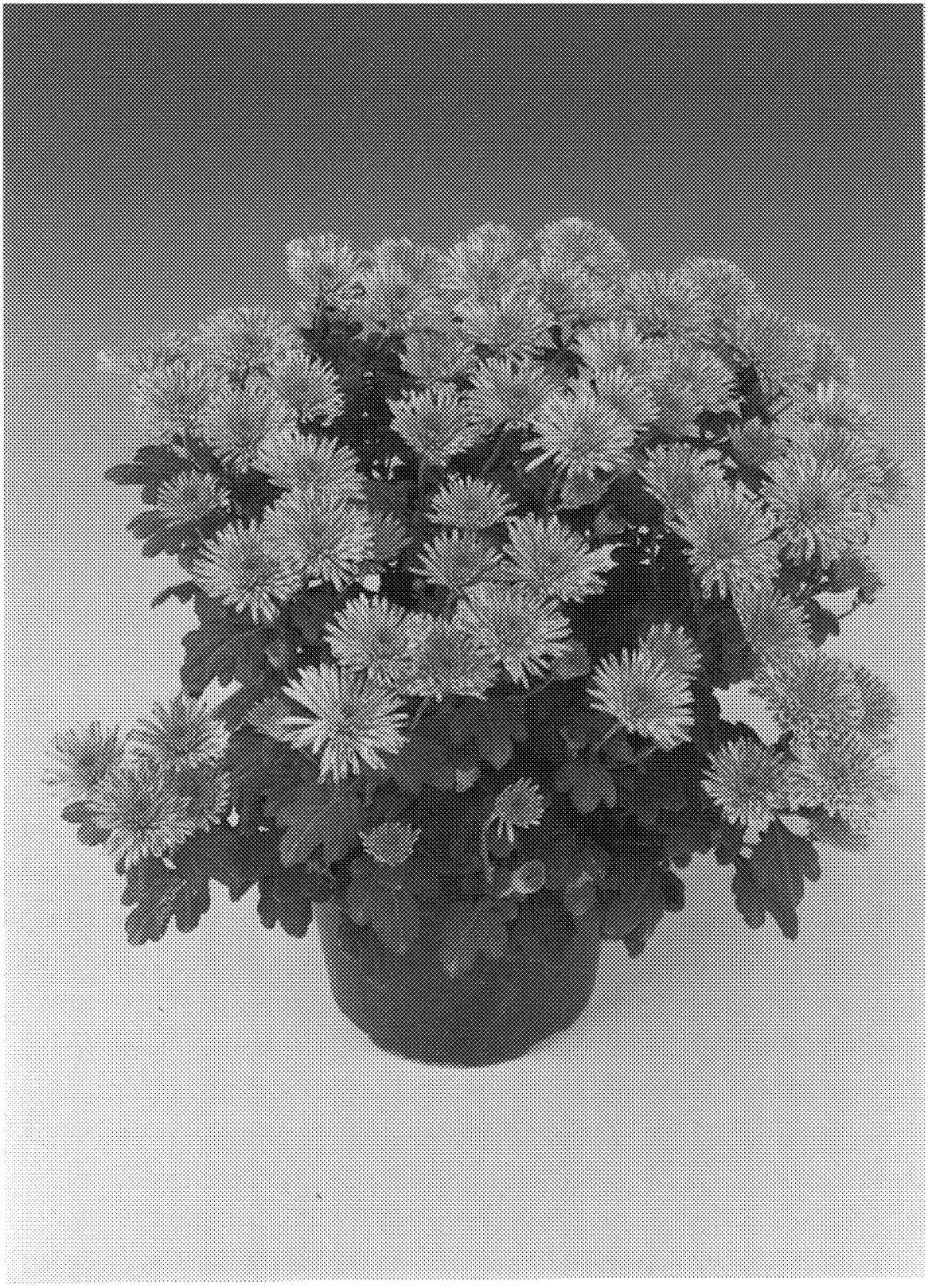
FIG. 1 is a whole plant view of the new cultivar grown in a pot.
Figure 2:
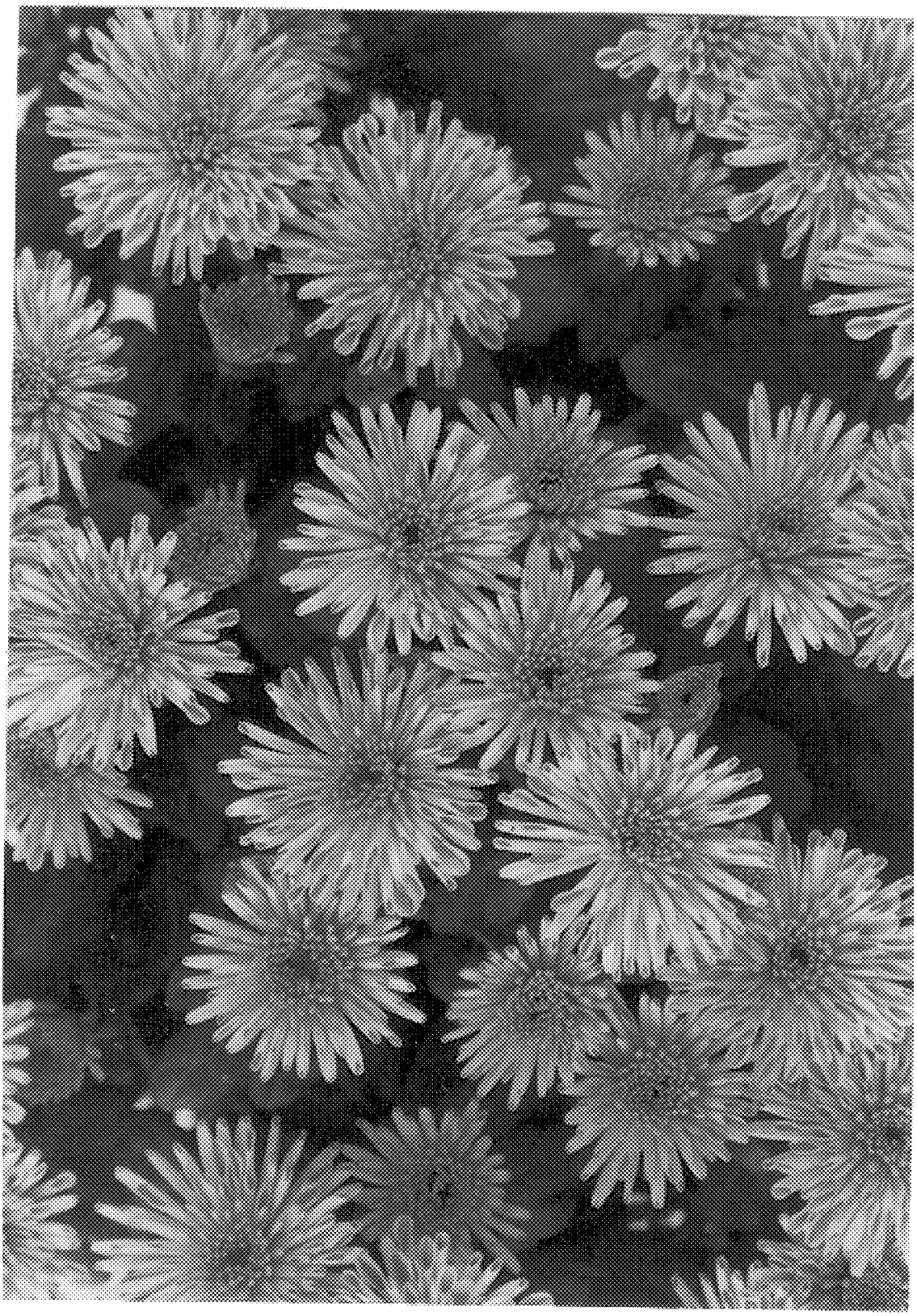
FIG. 2 is a closer view, showing inflorescence and foliage characteristics of the new cultivar in greater detail.

The following description of the new variety is of specimens grown in a greenhouse in Ventura County, Calif. 'Toucan' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once ten days after planting which results in about 4 breaks per pinch. It has been observed that the shelf life of 'Toucan' is about 18 days with the response time of about 6.5 weeks. No treatment with growth retardant is required. Useful growing conditions include night temperatures of about 64°–66° F., day temperatures of about 80°–85° F. and about 5,000 foot-candles of light.

Plant:

- *Habit.*—Short, spreading.
- *Height.*—About 20 cm.
- *Branching characteristics.*—Well branched.
- *Number of breaks from pinch.*—About 4.
- *Typical container sizes commercially grown in.*—4", 6", one gallon pots.
- *Length of lateral branches.*—About 12 cm.
- *Stem color.*—Near 147 C.

Foliage:

- *Leaf arrangement.*—Alternate.
- *Number of leaves per lateral branch.*—About 8 mature leaves.
- *Leaf size.*—Length: About 5.5 cm. Width: About 3.7 cm.
- *Leaf shape.*—Ovate.
- *Attachment.*—Petioled.
- *Leaf apex.*—Obtuse.
- *Base.*—Tapered.
- *Margin.*—Palmently lobed with infrequent mild serrations.
- *Aspect.*—Concave.
- *Surface.*—Top: Pubescent. Underside: Pubescent.
- *Petiole length.*—About 0.5 cm. Color: Near 138B. Other petiole characteristics: Winged.
- *Color.*—Mature leaf: Top: Near 137A. Bottom: Near 137C. Young leaf: Top: Near 137B. Bottom: Near 137D.

Flower:

- *Inflorescence form.*—Cyme.
- *Flower form.*—Spider daisy.
- *Number of blooms per branch.*—About 5.
- *Diameter of fully expanded bloom.*—About 6 cm.
- *Depth of fully expanded bloom.*—About 2 cm.
- *Longevity of individual blooms.*—About 18 days.
- *Sepal number.*—About 25. Color: Near 137B. General appearance of sepals: Concave, membranous, pubescent.

*Peduncle length.*—Terminal peduncle about 3.4 cm, lower most peduncle about 8 cm. Surface: Pubescent. Color: Near 146B. Strength: Weak.

*Flower bud shape.*—Sphere with flattened top. Diameter: About 0.8 cm. Height: About 0.5 cm.

*Ray florets.*—Number per flower: About 140. Shape: Tubular at base, becoming flared at tip, more pronounced in older florets. Apex: Obtuse. Base: Tapered, fused. Margin: Entire. Aspect: Mostly flat, reflexed at flared tip. Length: About 2.5 cm. Width: About 0.7 cm at flared tip, 0.3 cm at tapered base.

*Disc florets.*—Number per flower: About 40. Texture: Shiny. Shape: Cylindric. Margin: Entire. Length: About 0.3 cm. Width: About 0.1 cm.

*Fragrance.*—Light.

Flower color:

*General flower appearance.*—Light orange to pink upper ray florets with cream undersides.

*Ray florets, top side.*—Immature: Near 29D. Mature: Near 29D. Fading: Near 39D.

*Ray floret, under side.*—Immature: Near 29D. Mature: Near 36D. Fading: Near 20D.

*Disc florets.*—Mature: Near 31C.

*Changes as the flower ages.*—Yellow undertones become more apparent; eventually, flower turns a yellow/cream color; flower form becomes very flat.

Reproductive organs:

*Ray florets.*—Pistillate. Stigma shape: About 3 branched. Stigma color: Near 6A. Style length: About 0.3 cm.

*Disc florets.*—Stigma shape: About 2 branched. Stigma color: Clear. Style Length: About 0.2 cm. Anther length: About 0.1 cm. Pollen: Not present.

What is claimed is:

1. A new and distinct Chrysanthemum plant of the variety substantially as herein shown and described.

* * * * *